United States Patent
Meyer et al.

(10) Patent No.: US 10,408,778 B2
(45) Date of Patent: Sep. 10, 2019

(54) USE OF A POLYMER MIXTURE AS A SENSOR MIXTURE

(71) Applicant: NEXANS, Paris (FR)

(72) Inventors: Matthias Meyer, Nuremberg (DE); Jean Marc Gonnet, Nuremberg (DE); Anthony Combessis, Marseilles (FR)

(73) Assignee: NEXANS, Courbevoie (FR)

( * ) Notice: Subject to any disclaimer, the term of this patent is extended or adjusted under 35 U.S.C. 154(b) by 0 days.

(21) Appl. No.: 14/138,496

(22) Filed: Dec. 23, 2013

(65) Prior Publication Data
US 2014/0197853 A1   Jul. 17, 2014

(30) Foreign Application Priority Data

Jan. 17, 2013   (EP) .................................... 13305048

(51) Int. Cl.
*G01R 31/08* (2006.01)
*G01N 27/04* (2006.01)
*B82Y 30/00* (2011.01)
*G01N 33/44* (2006.01)

(52) U.S. Cl.
CPC ............ *G01N 27/041* (2013.01); *B82Y 30/00* (2013.01); *G01N 33/442* (2013.01)

(58) Field of Classification Search
CPC ....... G01R 31/08; G01N 27/041; B82Y 30/00
USPC ....................................................... 324/693
See application file for complete search history.

(56) References Cited

U.S. PATENT DOCUMENTS

| | | | | |
|---|---|---|---|---|
| 3,451,944 A | * | 6/1969 | Finch | ............................ 502/413 |
| 4,328,139 A | * | 5/1982 | Simons | ......................... 524/495 |
| 5,051,590 A | * | 9/1991 | Kern et al. | ............... 250/339.04 |
| 5,306,739 A | * | 4/1994 | Lucey | .............................. 522/42 |
| 2002/0041744 A1 | * | 4/2002 | Anelli | .................. G02B 6/4433 385/112 |
| 2002/0194934 A1 | * | 12/2002 | Taylor | ..................... G01L 1/205 73/862.046 |
| 2005/0268734 A1 | | 12/2005 | Watkins et al. | |
| 2008/0307909 A1 | * | 12/2008 | Watkins et al. | ................. 73/866 |
| 2009/0060832 A1 | * | 3/2009 | Zhou et al. | ................ 423/658.2 |
| 2010/0078194 A1 | * | 4/2010 | Bhatt et al. | ............. 174/110 SR |
| 2012/0001128 A1 | | 1/2012 | Kim et al. | |

FOREIGN PATENT DOCUMENTS

| | | |
|---|---|---|
| CN | 101283027 | 10/2008 |
| CN | 202495286 | 10/2012 |
| CN | 202495286 U | * 10/2012 |

OTHER PUBLICATIONS

Miscellaneous incoming document.

* cited by examiner

*Primary Examiner* — Huy Q Phan
*Assistant Examiner* — Zannatul Ferdous
(74) *Attorney, Agent, or Firm* — Sofer & Haroun, LLP

(57) ABSTRACT

A polymer mixture is provided suitable for use in a cable as a sensor polymer mixture for determining the mechanical and/or electrical stability or aging of a cable. The method may use the determination of changes in the polymer mixture, especially for determination of the aging and/or stability, for example as a measure for estimation of the wear or the remaining service life of a cable having the polymer mixture.

22 Claims, 1 Drawing Sheet

USE OF A POLYMER MIXTURE AS A SENSOR MIXTURE

RELATED APPLICATION

This application claims the benefit of priority from European Patent Application No. 13 305 048.4, filed on Jan. 17, 2013 the entirety of which is incorporated by reference.

BACKGROUND

Field of the Invention

The invention relates to a polymer mixture suitable for use as a sensor mixture.

A polymer mixture of this kind is to be used to determine the mechanical and/or electrical stability or aging of a cable. The corresponding sensor mixture may extend along the cable and form a component of the cross section of an extruded layer of the cable.

Description of Related Art

US 2012/0001128 A1 discloses a semiconductor mixture intended for high-voltage cables, which, with 100 parts by weight of a base polyolefin, contains 0.5 to 2.15 parts by weight of carbon nanotubes and 0.1 to 1 part by weight of a peroxidic crosslinker. The corresponding material is intended for use as an inner conductive layer which surrounds the conductor of a high-voltage cable and as an outer conductive layer which surrounds the insulation thereof.

EP 1 490 672 B1 describes a method for determining the stability of a polymer mixture in a cable by measuring the resistance or the conductivity of another polymer mixture containing 25% by weight of carbon black or metal particles as conductive constituents. Changes in resistance over time are used as a measure of aging, since the aging leads to compaction of the conductive constituents through shrinkage. The polymer mixture comprising conductive constituents may be arranged in the manner of a filament along the cable, in which case the resistance is measured along the polymer mixture.

OBJECTS AND SUMMARY

The problem addressed by the invention is that of providing an alternative polymer mixture for use as a sensor mixture and preferably that of providing an alternative method for determining changes in the polymer mixture, preferably that of providing alternative cables comprising the polymer mixture.

The invention solves this problem in accordance with the features of patent claim 1 through use of a polymer mixture comprising or consisting of at least one polymer, inorganic fillers, processing aids, 0.2 to 6% by weight of carbon nanotubes, optionally plasticizers, optionally a crosslinking system and optionally dyes.

For the sensor mixture, proportions of the constituents in % by weight are stated in relation to the overall mixture, unless indicated otherwise.

The polymer is, for example, polyalkylene, polypropylene, polyethylene (PE), preferably low-density PE (LDPE), polyethylene-vinyl acetate (EVA), polyurethane and mixtures of these, and is present, for example, to an extent of up to 60% by weight, preferably to an extent of 20 to 50% by weight.

Inorganic fillers are, for example, chalk and/or kaolin, for example to an extent of 5 to 60% by weight, and flame retardants, especially selected from aluminum trihydroxide (ATH), for example having a particle size $d_{50}$ of 1.7 to 2.1 µm and a BET surface area of 3 to 5 m$^2$/g, for example to an extent of 10 to 60% by weight, preferably to an extent of 40 to 50% by weight.

An example of an aging stabilizer which may be present, for example, to an extent of 0.3% by weight is tetrakis (methylene(3,5-di-(tert)-butyl-4-hydrocinnamate))methane (available as Irganox 1010).

The crosslinking system may include, for example, peroxide and/or ZnO, in which case the sensor mixture is crosslinked after or before arrangement on or in a cable, for example by heating and/or irradiation after extrusion thereof. The sensor mixture can be arranged by extrusion as a component of a polymer layer of the cable, for example as part of the cross section of the sheath and/or of an inner sheath layer, in which case the sensor mixture especially extends over the full length of the cable and forms a filament which extends along the cable as part of the sheath and/or of the inner sheath layer. Alternatively, the sensor mixture may be arranged as a filament which extends along the cable within the sheath.

The carbon nanotubes have, for example, an average diameter of 8-10 nm, preferably of 9.5 nm, especially with an average length of 1 to 5 .mu.m, preferably 1.4 to 1.6 .mu.m, especially 1.5 .mu.m, preferably with a carbon content of at least 90%, the remainder being metal oxides. Carbon nanotubes have, for example, a BET surface area of 200 to 400 m$^2$/g, preferably of 250 to 300 m$^2$/g.

It has been found that the sensor mixture can be formed by extrusion to filaments and then optionally crosslinked, and has electrical properties adequate for the detection of aging-dependent changes, especially a sufficient conductivity. Advantageously, a content of carbon nanotubes in the sensor mixture of 0.2 to 6% by weight, preferably 0.4 to 4 or to 2% by weight, is sufficient to impart to the mixture electrical properties which change measurably as a function of aging.

This low content of conductive constituents compared, for example, to the carbon black content of EP 1490672 B1 has the advantage that this constituent alters the properties to an only slight to insignificant extent compared to a polymer mixture identical apart from the carbon nanotubes, especially in relation to the aging characteristics. It is therefore preferable that the sensor mixture is identical to the polymer mixture of a constituent of the cable, especially identical to the polymer mixture of the sheath or of an inner sheath which additionally comprises the carbon nanotubes. In this embodiment, the aging characteristics of the sensor mixture correspond particularly to the aging characteristics of the polymer mixture of the sheath or of an inner sheath of the cable, and the content of carbon nanotubes which constitutes the sensor mixture having the constituents of the polymer mixture of the sheath or of an inner sheath endows the sensor mixture or the filament of the sensor mixture with electrical properties in which changes are measurable with the device or are measured in the method as a measure of the aging.

The sensor mixture has essentially the same mechanical properties as, or slightly altered mechanical properties with respect to, a polymer mixture identical except for the carbon nanotubes. Therefore, one advantage of the sensor mixture or of a cable having at least one filament of the sensor mixture is that the mechanical properties of the cable are not significantly worsened, if at all. This is of significance especially for embodiments in which a filament of the sensor mixture is formed on the outer surface of the sheath or as a component of the cross section within the sheath or an inner sheath.

The method for determining the stability of a cable comprising the sensor mixture, especially in the form of a filament of the sensor mixture which extends along the cable, includes the determination of the change in at least one electrical property of the sensor mixture, which is, for example, the conductivity, the resistance, the capacity and/or the dissipation factor.

It has been found that the sensor mixture shows significant changes in electrical properties dependent on influences which bring about aging. Preferably, the changes in electrical properties of the sensor mixture are greater than in a polymer mixture which, rather than the 0.2 to 6% by weight, for example, of carbon nanotubes according to the invention, contains 25% carbon black and otherwise has an identical composition.

In a first embodiment of the cable, the sensor mixture is arranged along the cable in the form of at least one filament which extends along the cable, the ends of which are electrically connected to a measurement unit. The sensor mixture is preferably arranged along the cable in the form of two or more filaments which extend along the cable, one end of each being electrically connected to a measurement unit in a first longitudinal section of the cable, and the ends thereof arranged in a second longitudinal section of the cable, spaced apart from the first longitudinal section, being electrically connected to one another. Preferably, the first longitudinal section is a first end of the cable and the second longitudinal section the second, spaced-apart end thereof. The filaments may be arranged within the sheath or an inner sheath and may make up a component of the cross section of the sheath or of an inner sheath.

For this embodiment, the sensor mixture may be co-extruded, for example, with the polymer mixture of the sheath or of the inner sheath, for example by means of a die with a strip distributor to which the sensor mixture is fed, such that the sensor mixture forms a strip in the polymer mixture of the sheath or of the inner sheath.

Alternatively, the sensor mixture can be extruded to a filament arranged within the sheath, for example by conducting the filament together with the elements of the cable to be arranged within the sheath through an extruder die, by means of which the polymer mixture of the sheath is extruded around these elements of the cable. For instance, the at least one filament may be stranded with the leads of the cable and/or be placed into a gap between the leads and insert-molded with the polymer material of an inner sheath and/or sheath.

In a second embodiment, the sensor mixture forms a sensor element in which the sensor mixture encompasses at least two conductors. Preferably, the sensor element has at least two conductors which are arranged at a distance within the sensor mixture and form contacts with the sensor mixture, especially over the full length thereof. Preferably, the conductors are arranged parallel to one another within the sensor mixture, in which case the sensor mixture especially takes the form of a filament in which at least two conductors are arranged spaced apart from one another and parallel to the longitudinal axis of the filament. In this embodiment, in which the sensor mixture with at least two spaced-apart conductors forms a sensor element, the sensor mixture is preferably arranged along the cable, for example on the outer surface of the cable sheath and/or within the cable sheath. In the case of arrangement of the sensor element within the cable sheath, it may be arranged together with the further elements of the cable which are encompassed by the sheath and insert-molded with a polymer mixture of the sheath. The sensor element may, as also described in relation to the first embodiment, be stranded with the leads and/or placed into the gaps thereof.

In the second embodiment, for measurement, each conductor of the sensor element arranged within the sensor mixture is connected to a measurement unit. In this embodiment, the measurement unit is preferably set up for measurement or determination of the capacity and/or the dissipation factor.

It has been found that the electrical properties of the sensor mixture are greatly influenced by increases in temperature. For example, the conductivity of the sensor mixture can be increased more quickly or more significantly by increases in temperature than is brought about by the aging, which causes, for example, shrinkage and/or embrittlement.

Accordingly, a cable preferably has, in addition to the sensor mixture, a temperature sensor and further preferably an evaluation unit set up to store temperature measurements and correlate them with the measurements for electrical properties of the sensor mixture. Further preferably, such an evaluation unit has data for a correlation between temperature measurements and electrical properties determined beforehand for the same sensor mixture, and is set up to include the correlation determined beforehand in the evaluation of the measurements for the electrical property of the sensor mixture as a function of the temperature measurements. The inclusion of the correlation of the temperature measurements determined beforehand in the evaluation of the measurements for the electrical property of the sensor mixture increases the accuracy of the determination of the aging by influences which are not caused by increases in temperature.

A preferred temperature sensor is an optical fiber, for example a glass fiber or optical fiber, present longitudinally within the cable. Preference is given to an optical fiber arranged adjoining the sensor mixture. For example, the optical fiber in the second embodiment of the sensor mixture may be arranged as a sensor element within the sensor mixture, for example parallel to the conductors of the sensor element. Such an optical fiber is connected, for example, to an optical detector set up for measurement of the optical properties, especially for measurement of the Raman scatter which is produced, for example, by injection of laser radiation into the optical fiber. Accordingly, the optical fiber may be provided with a laser for injection of laser radiation into the fiber, and with an optical detector arranged especially at the end of the optical fiber into which the laser radiation is injected. Preference is given to an optical fiber whose optical properties are only temperature-dependent. For example, it is possible to use an optical fiber having high stability to radioactive radiation, for example having a high OH content, with fluorine and/or bromine doping. One advantage of an inventive cable having an optical fiber in addition to the sensor mixture is that the optical fiber, under radioactive irradiation, undergoes a change in the optical properties thereof, for example haze and/or damping thereof. Therefore, in the process, the optical measurements can be used to determine the proportion of aging which is caused by radioactive radiation onto the cable. Accordingly, the evaluation unit may be set up to use the optical measurements which indicate radioactive irradiation of the cable to determine aging of the cable. Such an optical fiber preferably has a glass composition whose optical properties can be varied by radioactive irradiation, for example $\gamma$ radiation, especially independently of temperature. Such optical fibers are, for example, those having a low content of fluorine and/or of bromine, those composed of pure silicon dioxide, and/or those having a low OH content. Accordingly, the cable may include an optical fiber whose optical properties are temperature-dependent and/or an optical fiber whose optical properties can be varied by radioactive radiation. These properties, for example haziness, can be determined as damping in dB/km.

Preferably, the detector of each optical fiber is connected to an evaluation unit which has stored predetermined measurement data which contain the correlation of the measurements for the temperature and/or for radioactive radiation with the aging of the cable or at least of a polymer mixture of the cable, especially sheath mixture and/or the sensor mixture.

BRIEF DESCRIPTION OF THE DRAWINGS

The invention is now described more specifically using illustrative sensor mixtures and with reference to the figures, which show, in schematic form, in FIG. 1, an illustrative sensor element,
in FIG. 2, an execution of a cable sheath,
in FIG. 3, a cross section through one embodiment of a cable sheath with a sensor element, and
in FIG. 4, a cross section through a further embodiment of a cable sheath with a sensor element.

DETAILED DESCRIPTION

Figure 1:
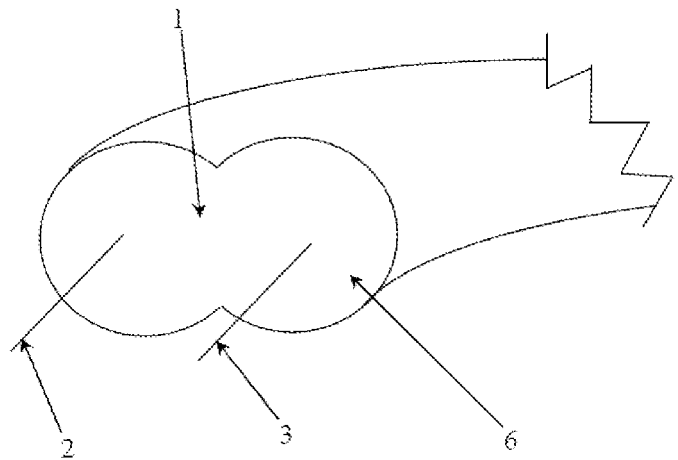

As a simple embodiment of the sensor mixture, carbon nanotubes (average diameter about 9.5 nm, an average length about 1.5 .mu.m, 90% carbon, 10% metal oxides, BET surface area 250-300 m$^2$/g) were mixed in mixture 1) to an extent of 2.1% by weight in 97.9% by weight of LDPE, and in mixture 2) to an extent of 6.5% by weight in 93.5% by weight of LDPE, and shaped by extrusion.

The measurement of the electrical resistance for mixture 1) gave the following values on aging at 100° C.:

| | Electrical resistance (ohms) | Elongation at break (%) |
|---|---|---|
| On day 0 | 1.52 × 10$^{11}$ | 143 |
| Day 7 | 7.34 × 10$^{10}$ | not determined |
| Day 45 | 8.55 × 10$^8$ | 51 |

For mixture 1), a change in the resistance as a function of aging was measured. The aging was determined as the decrease in the elongation at break as a representative parameter for strength.

For mixture 2), no change in the resistance with aging was found. This is attributed to the fact that the content of carbon nanotubes was too high to show aging-related changes in electrical resistance.

The following sensor mixtures show a measurable change in the electrical properties as a function of aging:

| Ingredient | Mixture | | | | | | | | | | |
| | 3) | 4) | 5) | 6) | 7) | 8) | 9) | 10) | 11) | 12) | 13) |
|---|---|---|---|---|---|---|---|---|---|---|---|
| CNT | 1.8 | 1.8 | 0.2 | 0.7 | 1.0 | 1.6 | 2.3 | 3 | 4 | 1.8 | 1.8 |
| LDPE | 22 | — | — | 22 | 22 | 22 | 22 | 22 | 22 | 48 | 48 |
| EVA | 26 | 48 | 49.6 | 27.1 | 26.8 | 26.2 | 25.5 | 24.8 | 23.8 | — | 44 |
| ATH | 44 | 44 | 44 | 44 | 44 | 44 | 44 | 44 | 44 | 44 | — |
| AS | 1 | 1 | 1 | 1 | 1 | 1 | 1 | 1 | 1 | 1 | 1 |
| Peroxide | 0.1 | 0.1 | 0.1 | 0.1 | 0.1 | 0.1 | 0.1 | 0.1 | 0.1 | 0.1 | 0.1 |
| Processing aid | 5.1 | 5.1 | 5.1 | 5.1 | 5.1 | 5.1 | 5.1 | 5.1 | 5.1 | 5.1 | 5.1 |

CNT = carbon nanotubes, AS = aging stabilizer

Using the example of mixture 3), it is possible to show that the content of carbon nanotubes does not worsen the mechanical properties. The mechanical properties of mixture 3) compared to mixture C3), which otherwise had the same composition without the content of carbon nanotubes, are shown hereinafter:

| Property | Mixture 3) | Mixture C3) |
|---|---|---|
| Elongation at break (%) | 123 | 160 |
| Tensile strength (MPa) | 12.8 | 11 |
| Elongation after 7 days at 100° C. (%) | 104 | — |
| Tensile strength after 7 days at 100° C. (MPa) | 13.7 | — |

FIG. 1 shows a sensor element 6 composed of a sensor mixture 1 in which two spaced apart conductors 2, 3 are each arranged in parallel to the longitudinal axis of the extruded sensor mixture. The ends of each of the conductors 2, 3 should form contacts with a measurement unit.

In one test, for a sensor element of total length 5 m according to FIG. 1, the change in the electrical resistance was measured. In this test, it was found that the resistance increased with increasing aging as a result of thermal stress (oven aging). The sensor mixture had the composition 3) and contained 1.8% by weight of carbon nanotubes.

The resistance was determined between the two conductors 2, 3 with a hand-held measuring instrument. The resistance was 167.6 ohms before the aging, 819 ohms after oven aging at 100° C. for 7 d, and 11 160 ohms after 100° C. for 40 d. In a corresponding test with an originally identical sensor element, the resistance after oven aging at 80° C. for 7 d was measured at 658 ohms, and that after oven aging at 80° C. for 40 d was measured at 1608 ohms. The resistance of the two conductors 2, 3 themselves had not changed significantly as a result of the oven aging, and so the sensor mixture in this test showed an increase in the resistance through aging.

Figure 2:
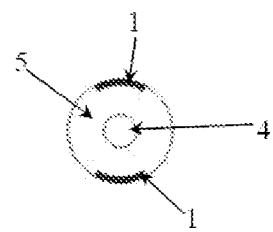

FIG. 2 shows a schematic of the cross section through a cable having two spaced-apart filaments of a sensor mixture extruded as a component of the cross section of the sheath 5. This corresponds to the first embodiment, in which a filament or ends of mutually connected filaments of sensor mixture should be connected to a measurement unit.

Figure 3:
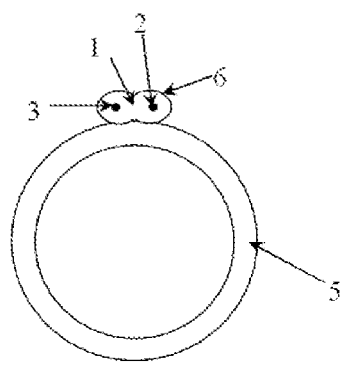
Figure 4:
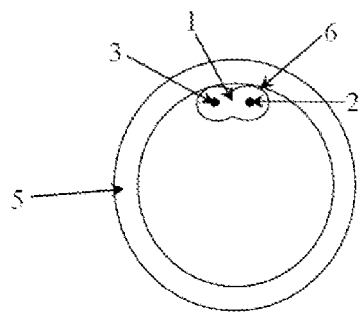

FIGS. 3 and 4 show neither leads nor inner sheaths of the cable.

FIG. 3 shows a cable in which a sensor element 6 is arranged on the outer surface of the sheath 5.

FIG. 4 shows a cable in which sensor element 6 is arranged within the sheath 5, produced, for example, by, in the process for production, insert-molding the elements of the cable encompassed by the sheath, including the sensor element 6, with a polymer mixture which forms the sheath.

LIST OF REFERENCE NUMERALS 1 sensor mixture
2 conductor
3 conductor
4 lead
5 sheath
6 sensor element

The invention claimed is:

1. Sensor device for a cable, the cable having at least one conductor inside of a sheath and/or an inner sheath, said sensor device being designed for determining the ageing of said cable, said sensor device comprising:
a polymer sensor mixture being a separate structure from both said sheath and/or said inner sheath of said cable and said at least one conductor, said polymer sensor mixture being arranged along said cable sheath or inner sheath, said separate structure of said polymer sensor mixture including, entirely within it, at least two additional spaced-apart conductors, said at least two additional spaced-apart conductors being arranged at a distance apart from one another within the separate structure of said polymer sensor mixture and having contact with said polymer sensor mixture, wherein said polymer sensor mixture, with said two additional spaced apart conductors therein, takes the form of a filament,
said at least two additional spaced-apart conductors within said polymer sensor mixture are parallel to one another and to the longitudinal axis of the filament;
said separate structure of polymer sensor mixture, with said at least two additional conductors, forming a sensor element disposed on an outside or an inside of said sheath or inner sheath, and
a measurement unit, wherein each of said two additional conductors of said sensor element arranged within the sensor mixture are connected to said measurement unit,
wherein said polymer sensor mixture is a polymer mixture having:
at least one polymer;
inorganic fillers;
processing aids;
0.2 to 6% by weight of carbon nanotubes;
optionally plasticizers;
optionally a crosslinking system; and
optionally dye.

2. Sensor device according to claim 1, wherein the carbon nanotubes have an average diameter of 8-10 nm, an average length of 1 to 5 µm, a carbon content of at least 90%, the remainder being metal oxides, and a BET surface area of 200 to 400 $m^2/g$.

3. Sensor device according to claim 1, wherein the polymer mixture contains up to 60% by weight of flame retardant.

4. Sensor device according to claim 1, wherein at least one optical fiber, arranged along the cable, is connected to an optical detector from which the measurements are sent to an evaluation unit connected to said measurement unit, said evaluation unit being set up to correlate measurements from the measurement unit with the measurements from the optical detector, at least one optical fiber having a glass composition whose optical properties are temperature-dependent and/or at least one optical fiber having a glass composition whose optical properties can be varied by radioactive irradiation.

5. Method for determining the aging of a cable constructed with a sensor device according to claim 1, wherein measurements of the conductivity, the resistance, the capacity and/or the dissipation factor of the sensor mixture are determined.

6. Method according to claim 5, wherein an optical fiber arranged along the cable has temperature-dependent optical properties, and measurements of the temperature-dependent optical properties are taken, and/or in that the cable contains an optical fiber which is arranged along the cable and has optical properties dependent on radioactive irradiation, and measurements of the optical properties thereof dependent on radioactive irradiation are taken.

7. Method according to claim 5, wherein the measurements of the conductivity, the resistance, the capacity and/or the dissipation factor of the sensor mixture, measurements of temperature-dependent optical properties and/or measurements of optical properties dependent on radioactive irradiation are compared in an evaluation unit with data which contain a predetermined correlation of the aging of at least one polymer mixture in the cable with this measurement.

8. Sensor device according to claim 1, wherein the polymer mixture has 0.2 to 4% by weight of carbon nanotubes.

9. Sensor device according to claim 1, wherein the sensor element is arranged on the outer surface of said cable sheath and/or within said cable sheath.

10. Sensor device according to claim 1, wherein said at least two spaced-apart conductors are embedded in said polymer sensor mixture.

11. Sensor device according to claim 1, further comprising said cable.

12. Sensor device for a cable, the cable having at least one conductor and a sheath or an inner sheath, said sensor device being designed for determining the ageing of said cable, said sensor device comprising:
a polymer sensor mixture arranged as separate polymer structure within the cross section of said sheath or inner sheath and running along the length of said cable, said polymer sensor mixture being in the form of at least two or more separate polymer filaments, each of which extend separately from, but within said sheath or inner sheath, substantially along the entire length of the cable, the filaments making up a component of the cross section of said sheath or of said inner sheath along the entire length of the cable, and
a measurement unit, wherein said component is connected to said measurement unit at ends of said filaments,
wherein said polymer sensor mixture is a polymer mixture having:
at least one polymer;
inorganic fillers;
processing aids;
0.2 to 6% by weight of carbon nanotubes;
optionally plasticizers;
optionally a crosslinking system; and
optionally dye.

13. Sensor device according to claim 12, wherein one end of each filament is electrically connected to said measurement unit in a first longitudinal section of said cable, and the ends thereof arranged in a second longitudinal section of said cable, spaced apart from the first longitudinal section, are electrically connected to one another.

14. Sensor device according to claim 12, wherein said at least two filaments are spaced-apart within said sheath or said inner sheath.

15. Sensor device according to claim 12, wherein the carbon nanotubes have an average diameter of 8-10 nm, an average length of 1 to 5 µm, a carbon content of at least 90%, the remainder being metal oxides, and a BET surface area of 200 to 400 $m^2/g$.

16. Sensor device according to claim 12, wherein the polymer mixture contains up to 60% by weight of flame retardant.

17. Sensor device according to claim 12, wherein at least one optical fiber, arranged along the cable, is connected to an optical detector from which the measurements are sent to an evaluation unit connected to said measurement unit, said evaluation unit being set up to correlate measurements from the measurement unit with the measurements from the optical detector, at least one optical fiber having a glass composition whose optical properties are temperature-dependent and/or at least one optical fiber having a glass composition whose optical properties can be varied by radioactive irradiation.

18. Method for determining the aging of a cable constructed with a sensor device according to claim 1, wherein measurements of the conductivity, the resistance, the capacity and/or the dissipation factor of the sensor mixture are determined.

19. Method according to claim 18, wherein an optical fiber arranged along the cable has temperature-dependent optical properties, and measurements of the temperature-dependent optical properties are taken, and/or in that the cable contains an optical fiber which is arranged along the cable and has optical properties dependent on radioactive irradiation, and measurements of the optical properties thereof dependent on radioactive irradiation are taken.

20. Method according to claim 18, wherein the measurements of the conductivity, the resistance, the capacity and/or the dissipation factor of the sensor mixture, measurements of temperature-dependent optical properties and/or measurements of optical properties dependent on radioactive irradiation are compared in an evaluation unit with data which contain a predetermined correlation of the aging of at least one polymer mixture in the cable with this measurement.

21. Sensor device according to claim 12, wherein the polymer mixture has 0.2 to 4% by weight of carbon nanotubes.

22. Sensor device according to claim 1, further comprising said cable.

* * * * *